United States Patent [19]

Degen et al.

[11] Patent Number: 5,282,971
[45] Date of Patent: Feb. 1, 1994

[54] POSITIVELY CHARGED POLYVINYLIDENE FLUORIDE MEMBRANE

[75] Inventors: Peter J. Degen, Huntington; Joseph Lee, South Setauket, both of N.Y.

[73] Assignee: Pall Corporation, East Hills, N.Y.

[21] Appl. No.: 64,229

[22] Filed: May 11, 1993

[51] Int. Cl.⁵ .................... B01D 63/08; B01D 71/34
[52] U.S. Cl. .................... 210/645; 210/654; 210/321.75; 210/321.84; 210/500.37; 210/500.42
[58] Field of Search ............... 210/634, 644–646, 210/649–654, 321.6, 321.72, 321.75, 321.84, 321.85, 321.76, 500.27, 500.37–500.39, 500.36, 500.42

[56] References Cited

U.S. PATENT DOCUMENTS

| | | |
|---|---|---|
| 3,083,118 | 3/1963 | Bridgeford . |
| 3,698,931 | 10/1972 | Horowitz . |
| 3,723,306 | 3/1973 | Bridgeford . |
| 3,862,059 | 1/1975 | Greco et al. . |
| 4,230,573 | 10/1980 | Kilty et al. . |
| 4,594,202 | 6/1986 | Pall et al. . |
| 4,678,813 | 7/1987 | Itoh et al. . |
| 4,693,985 | 9/1987 | Degen et al. . |
| 4,702,840 | 10/1987 | Degen et al. . |
| 4,702,947 | 10/1987 | Pall et al. . |
| 4,726,901 | 2/1988 | Pall et al. . |
| 4,758,239 | 7/1988 | Yeo et al. . |
| 4,849,106 | 7/1989 | Mir . |
| 4,871,594 | 10/1989 | Bister et al. . |
| 4,943,373 | 7/1990 | Onishi et al. . |
| 4,968,533 | 11/1990 | Gsell . |
| 4,976,897 | 12/1990 | Callahan et al. . |
| 5,019,260 | 5/1991 | Gsell et al. . |
| 5,019,261 | 5/1991 | Stengaard . |

FOREIGN PATENT DOCUMENTS

| | | |
|---|---|---|
| 0099699 | 7/1983 | European Pat. Off. . |
| 0329303 | 2/1989 | European Pat. Off. . |
| 2016943 | 10/1979 | United Kingdom . |

Primary Examiner—Frank Sever
Attorney, Agent, or Firm—Leydig, Voit & Mayer

[57] ABSTRACT

A filter medium comprising a microporous polyvinylidene fluoride membrane and a polymer containing positively charged quaternary ammonium groups covalently bonded to the membrane, and a method of using the filter medium to treat a composition, particularly a biological or pharmaceutical composition such as an ophthalmic composition.

29 Claims, No Drawings

POSITIVELY CHARGED POLYVINYLIDENE FLUORIDE MEMBRANE

TECHNICAL FIELD OF THE INVENTION

The present invention relates to a positively charged microporous filter medium suitable for use in treating a variety of compositions, particularly pharmaceutical and biological solutions. The present inventive filter medium allows for the filtration of compositions to remove undesirable contaminants such as bacteria, while allowing desirable positively charged species such as preservatives, bacteriostats, and the like to pass through the filter with the filtrate.

BACKGROUND OF THE INVENTION

Microporous membranes are well-known in the art. Such membranes have been used to ultrapurify water for use in making semiconductors, to filter paint compositions, to purify pharmaceuticals, and to perform a number of other widely divergent functions. Microporous membranes can have pore sizes ranging from about 0.01 to over 10 $\mu$m; thus, they are suitable for removing particles of a variety of sizes.

Filters are typically used to remove suspended contaminants from fluids to provide for the passage of the clarified fluid (filtrate). A filter can achieve fluid clarification by different mechanisms. Suspended contaminants can be removed through mechanical sieving wherein particles larger than the pore rating of the filter medium are removed from the fluid. With this mechanism, filtration efficiency is essentially controlled by the size of the contaminant relative to the pore diameter of the filter medium.

Another mechanism by which a filter can achieve fluid clarification is through adsorption of suspended contaminants onto the filter surface. Removal of contaminants by this mechanism is controlled by the surface characteristics of the suspended contaminants and by the filter medium itself. Conventional filter media, however, adsorb many different particles without discretion. This often is undesirable in that many filtering applications require certain compounds to remain in the filtrate instead of adsorbing onto the surface of the filter medium. For example, in the filtering of pharmaceutical and biological compositions to remove contaminants, it is typically undesirable to remove preservatives, bacteriostats, and the like from the composition.

In the filtering of compositions, many different materials have been used to prepare filter media. Of particular usefulness have been polymers such as polyamides, polyesters, polyolefins, and the like. Many of the polymers which provide desirable structural characteristics, such as polyolefins, however, are hydrophobic and are not well-suited for filtering aqueous media at low fluid pressures. In order to render such filter media more suitable for aqueous filtration, techniques have been developed to render the surfaces of the filter media hydrophilic. For example, a polyvinylidene fluoride (PVDF) membrane, which is inherently hydrophobic, may be treated with a strong alkali solution in combination with an oxidizing agent to render it hydrophilic. It is believed, in this particular technique, that the base liberates hydrogen fluoride, and the oxidizing agent introduces a polar group onto the backbone of the PVDF, rendering the surface hydrophilic. This method has the disadvantage, however, of causing the filter medium to have a high affinity for positively charged preservatives, bacteriostats, and the like in fluids treated with the filter medium, thereby retaining such species rather then desirably passing them through with the filtrate.

Attempts at ameliorating such disadvantages have not met with success. For example, an excess number of positively charged quaternary ammonium compounds have been affixed by ionic bonds to a PVDF filter medium in order to reduce the affinity of positively charged preservatives, bacteriostats, and the like for the PVDF filter medium. This filter medium, however, has the drawback that the quaternary ammonium compounds are susceptible to leaching out, thereby rendering such a filter medium unsuitable in applications where the amount of extractables is to be kept to a minimum.

Other filter media have been disclosed as useful in the removal of bacterial endotoxins and heparin from blood. These filter media are comprised of a substrate matrix to which has been bonded quaternary ammonium compounds. The substrate matrix may be prepared from any suitable material, such as a polyamide, polyester, polyolefin, polysulfone, polyarylene oxide, polyarylene sulfide, and unsaturated nitriles. Many of these filter media, however, are not well-suited for applications in which one desires positively charged species such as preservatives, bacteriostats, and the like to pass through the filter medium and remain in the filtrate. For example, polyamides treated with quaternary ammonium compounds undesirably retain such positively charged species.

An important industrial use of microporous filter media is in the manufacture of pharmaceutical and biological compositions, such as ophthalmic solutions. Ophthalmic solutions for contact lenses and medicinal eye treatments typically contain a small amount (approx 0.01%) of preservatives such as benzalkonium chloride (BAK), quaternary ammonium compounds, and the like. During filtration, these preservatives adsorb onto the surface of a conventional filter medium to various extents, thereby decreasing the concentration of the preservatives in the filtrate to undesirable and/or unknown levels. Such adsorption represents a significant drawback to conventional filter media.

Thus, notwithstanding the wide variety of microporous filter media known in the art, there exists a need for a hydrophilic filter medium that is suitable for use in pharmaceutical and biological applications in which filtration of compositions is required to remove impurities such as bacteria while allowing for the passage of desirable positively charged species such as BAK along with the filtrate. The present invention provides such as a filter medium.

It is an object of the present invention to provide a microporous filter medium that is hydrophilic and is thus suitable for filtering aqueous media without the application of substantial pressure. It is another object of the present invention to provide a filter medium that has a positively charged surface with minimal susceptibility to the extraction of the agent that renders the membrane positively charged. It is a further object of the present invention to provide a filter medium that is suitable for filtering pharmaceutical and biological compositions such as ophthalmic solutions wherein desirable positively charged species such as BAK pass through the filter medium and are present in the filtrate.

These and other objects and advantages of the present invention, as well as additional inventive features, will be apparent from the description of the invention provided herein.

BRIEF SUMMARY OF THE INVENTION

The present invention provides a filter medium comprising a microporous polyvinylidene fluoride membrane and a polymer containing positively charged quaternary ammonium groups covalently bonded to the membrane. The polymer containing quaternary ammonium groups is prepared from any suitable monomer(s), preferably diallyldimethylammonium chloride. The monomer containing quaternary ammonium groups is preferably polymerized with an acrylate, especially hydroxyethyl methacrylate, and the polymerization process and covalent bonding to the membrane is preferably effected by gamma radiation grafting. It has been found that, surprisingly, the present inventive microporous filter medium is quite useful in the treatment of pharmaceutical and biological compositions to remove undesirable contaminants while allowing other, desirable species to be retained in the filtrate.

The present invention also provides a method of treating compositions, particularly pharmaceutical and biological compositions, by filtering such compositions with the filter medium of the present invention. The present inventive method allows for the removal of undesirable contaminants from pharmaceutical and biological compositions, while allowing desirable positively charged species, such as preservatives, bacteriostats, and the like, to pass through the filter medium and thereby be present in the filtrate.

DETAILED DESCRIPTION OF THE PREFERRED EMBODIMENTS

The present inventive filter medium comprising a microporous polyvinylidene fluoride membrane and a polymer containing positively charged quaternary ammonium groups covalently bonded to the membrane. The present inventive treatment method comprises filtering compositions through such a filter medium.

Surprisingly, it has been found that the filter medium of the present invention is particularly suitable for use in filtering applications in which contaminants need to be removed from the composition without substantially removing desirable positively charged species, such as preservatives, bacteriostats, and the like, which preferably substantially remain in the filtrate. Such species include positively charged preservatives and bacteriostats, such as benzalkonium chloride (BAK), methyl paraben (MPB), propyl paraben (PPB), cetyl pyridium chloride (Cetamium ®), methyl benzothonium chloride (Hymamine ® 10X), and chlorohexidine (Nolvasan ®), particularly quaternary ammonium compounds.

Microporous Membrane

The microporous membrane is formed of polyvinylidene fluoride (PVDF) using conventional techniques known in the art. The microporous membrane may have any suitable pore size, preferably ranging from about 0.05 to about 5 μm, more preferably ranging from about 0.05 to about 0.45 μm.

Polymer Containing Quaternary Ammonium Groups

The polymer containing quaternary ammonium groups may o be any such polymer which imparts a positive charge to the microporous membrane. The polymer reduces the ability of the microporous membrane to adsorb preservatives, bacteriostats, and the like and preferably renders the microporous membrane hydrophilic.

The polymer containing quaternary ammonium groups may be prepared from any polymerizable ethylenically unsaturated monomer which either contains a quaternary ammonium group or which is capable of being converted to such a group. For example, the monomer may contain primary, secondary, or tertiary amino groups, which may be quaternized before grafting or which may be quaternized in situ after bonding to the membrane. Suitable monomers include the quaternized derivatives of aminoalkyl acrylates and methacrylates, quaternized aminoalkyl acrylamides and methacrylamides such as methacrylamidopropyl trimethylammonium chloride (MAPTAC), styrenic compounds, and vinylic compounds such as diallyldimethylammonium chloride (DADMAC).

DADMAC is especially preferred in the context of the present invention. It is the least toxic of the available quaternary materials, its linkage to the membrane is nonhydrolyzable, and it yields excellent results when filtering pharmaceutical and biological solutions containing preservatives, bacteriostats, and the like inasmuch as it allows these compounds to pass through the microporous membrane without significant adsorption onto the membrane.

The polymer will typically be prepared from one or more other monomers together with the quaternary ammonium compound. The polymer preferably is prepared from a quaternary ammonium compound in conjunction with one or more polar, hydrogen-bonding, nonionic, polymerizable ethylenically unsaturated monomers. Such a monomer may be completely inert or may contain functional groups which confer additional desired properties or exercise control over the surface properties already conferred by the quaternary ammonium groups, provided that these functional groups do not interfere with the functioning of the filter medium. Suitable additional monomers include polar, nonionic monomers such as hydroxyl-containing monomers, particularly acrylates and methacrylates, for example, hydroxypropyl acrylate (HPA), hydroxyethyl acrylate (HEA), diethylene glycol diacrylate (DEGDA), hydroxyethyl methacrylate (HEMA), polyethylene glycol dimethacrylate (PEGDM), hydroxypropyl methacrylate (HPMA), and diethylene glycol dimethacrylate (DEGDMA), which contain polar, hydrogen-bonding functionalities and tend to impart hydrophilicity to the microporous membrane. The monomers HPA and HEMA, most preferably HEMA, are used in conjunction with the quaternary ammonium group-containing monomer. The inclusion of a monomer having a hydrophobic moiety, such as methyl methacrylate, can be used, of course, to obtain precise control over the final hydrophilicity of the membrane by tempering the effect of monomers containing hydrophilic groups.

It is only required that the polymer contain sufficient quaternary ammonium groups to overcome the negative potential inherent on the surface of the microporous membrane. The required amount may be achieved by forming a thin polymer coating containing a large proportion of quaternary ammonium groups. It is undesirable to form a very thick coating on the microporous membrane because the polymer may partially block the pores of the membrane and reduce the permeability of the filter medium. Thus, it is desired that the polymer contain as high a proportion of quaternary ammonium groups as possible so as to enable the polymer coating to be as thin as possible while still counteracting the negative potential inherent in the microporous membrane. It is preferred that the polymer comprise at least about 50% by weight of the quaternary ammonium group-containing monomer, more preferably from about 50% by weight to about 85% by weight of the quaternary ammonium group-containing monomer. It is especially preferred that the polymer comprise about 50% by weight to about 70% by weight of quaternary ammonium group-containing monomer. The balance of the polymer will comprise the nonionic polar monomer. The content of nitrogen in the polymer is preferably at least about 4% by weight.

Membrane-Polymer Bonding

The filter medium of the present invention is preferably formed by contacting the microporous membrane with the monomers which polymerize to form the polymer containing quaternary ammonium groups in such a way that the polymer is covalently bonded to the microporous membrane. More preferably, the microporous membrane is exposed to ionizing radiation and then contacted with a grafting solution comprising polymerizable ethylenically unsaturated monomer or monomers, at least some of which contain quaternary ammonium groups, such that the monomer or monomers polymerize to form a polymer coating on all the fluid-contacting surfaces of the microporous membrane. The concentration of quaternary ammonium group-containing monomer in the grafting solution may be of any suitable amount, preferably about 1-50 vol. %, more preferably about 10-35 vol. %, particularly when the quaternary ammonium group-containing monomer is DADMAC and the solvent is water. If other monomers such as HEMA are used with the quaternary ammonium group-containing monomer, then the quaternary ammonium group-containing monomer is preferably present in an amount of about 1-50 vol. %, more preferably about 5-20 vol. %, and most preferably about 5-10 vol. %, and any other monomers are preferably present in an amount of about 0.1-5 vol. %, more preferably about 0.5-4 vol. %, and most preferably about 1-3 vol. %.

The volume ratio of quaternary ammonium group-containing monomers to other monomers in the grafting solution, when such other monomers are present, preferably is between about 20:1 to about 2:1. It is more preferred that the ratio be about 15:1 to about 3:1, and most preferred that the ratio be about 10:1.

To form the grafting solution, the monomer or monomers may be dissolved in any solvent or combination of solvents which is capable of dissolving all of the monomers together and which does not interfere with the formation of the polymer coating on the microporous membrane. The preferred solvent is water. If the monomers are not fully soluble in water, an amount of a water-miscible inert organic cosolvent such as 2-methylpropan-2-ol may be added in an amount sufficient to enable complete dissolution of the monomers.

The polymer containing quaternary ammonium groups is formed by exposing the microporous membrane to ionizing radiation in the presence of the monomer solution. Any source of ionizing radiation may be used, provided that the radiation is capable of initiating graft polymerization. Gamma radiation and electron beam radiation are preferred. Especially preferred is gamma radiation from a $^{60}Co$ source. Irradiation at any dose rate is acceptable provided it enables formation of a membrane having the desired surface properties and the membrane is not damaged by the radiation. Dose rates from about to about 1 to about 1,000 kilorads/hr and preferably from about 5 to about 100 kilorads/hr may be used. In general, higher dose rates can be effective in forming a polymer on substances which appear to react poorly with the quaternary ammonium group-containing monomer when no other comonomers are present. Total doses in the range of from about 0.05 to about 5 megarads, more typically in the range 0.2 to 2 megarads, are usually sufficient to effect the desired polymerization and bonding.

The microporous membrane may be contacted with the polymerizable monomer solution by any appropriate means, such as by immersion in the monomer solution. Alternatively, the monomer solution may be forced through the microporous membrane by the application of pressure across the membrane to initiate flow or to increase the efficiency of the wetting process. In any case, all the fluid-contacting surface area of the microporous membrane should be in contact with an excess of the monomer solution during formation of the filter medium to ensure complete coverage of the surface with the grafted polymer.

After irradiation and polymerization, the filter medium is washed with water to remove polymeric debris that is not bonded to the membrane. Any means of washing which causes water to flow across the entire membrane surface is appropriate, provided that it is carried out sufficiently to remove all the unbound debris. Particularly effective for washing the filter medium is flowing deionized water through the membrane for about 5 hours at a flow rate of about ⅛ gallon per minute (gpm) for 10 square feet of membrane surface area.

After washing, the filter medium may be dewatered and/or dried and subjected to any further processing. Drying conditions of up to about 100° C. for up to about 14 hours have been found satisfactory, although less time is usually sufficient to effect the desired drying of the filter medium.

Filter Elements

Any suitable filter element may be prepared using the filter medium of the present invention. In particular, filter cartridges may be prepared using the present inventive filter medium, either unsupported or interleaved with support layers, particularly nonwoven support layers which serve as support and drainage layers.

Pore Size Measurement

Pore sizes for the filter media described herein were determined using the $K_L$ test set forth in U.S. Pat. No. 4,340,479.

CWST Measurement

The critical wetting surface tension (CWST) of a porous medium is the surface tension between that of the liquid which is imbibed and that of the liquid which is not imbibed within a predetermined amount of time by the porous medium. Thus, liquids with surface tensions lower than the CWST of a porous medium will spontaneously wet the medium upon contact and, if the medium is porous, will flow through readily. On the other hand, liquids with a surface tension higher than the CWST of a porous medium may not flow through at all at low differential pressures and, at sufficiently high differential pressures, may flow through unevenly. As disclosed in U.S. Pat. No. 4,880,548, the CWST of a porous medium may be determined by individually applying drops of a series of liquids with surface tensions varying by 2 to 4 dynes/cm and observing the absorption or nonabsorption of each liquid over time.

The following examples further illustrate the present invention and, of course, should not be construed as in any way limiting its scope.

EXAMPLE 1

This example illustrates the preparation of the filter medium of the present invention. This example also compares the hydrophilicity of the present inventive filter medium with a similar filter medium to which has not been grafted a polymer containing quaternary ammonium groups.

Twenty feet of unsupported microporous polyvinylidene fluoride of two different pore sizes, 0.05 microns and 0.2 microns, were prewet with methanol and rolled with Reemay ® interleaf 2250 into a roll. Each of these rolls was introduced into a separate test tube containing 6 vol. % DADMAC, 1.5 vol. % PEGDM 600, and 92.5 vol. % deionized water. A vacuum was applied, and each of the test tubes was sealed with a stopper and irradiated in a $^{60}$Co vault at a dosage of 60,000 rad/hr for 30 hours at 80° F., for a total radiation dose of 1.8 Mrad. The grafted medium from each of the test tubes was washed in a deionized water trough for 4 hours to remove unreacted monomer, and dried at 100° C. for 10 minutes.

The hydrophilicity of each of these filter media was evaluated by determining the CWST of each of the filter media. The CWST values of the filter media of the present invention were then compared to the CWST of filter media prepared from untreated PVDF filter media of the same pore ratings. The obtained values for each of these various filter media are set forth below.

| Sample No. | Membrane | Monomer Formulation (aq. vol. %) | Pore Rating (microns) | CWST (dynes/cm) |
|---|---|---|---|---|
| 1 | PVDF | 6% DADMAC 1.5% PEGDM 600 | 0.20 | 75–81 |
| 2 | PVDF | 6% DADMAC 1.5% PEGDM 600 | 0.05 | 75–81 |
| 3 | PVDF | — | 0.20 | <36 |
| 4 | PVDF | — | 0.05 | <36 |

The filter media of the present invention (sample nos. 1–2) were found to be instantly wettable with water and far superior with respect to hydrophilicity as measured by CWST to untreated PVDF filter media of similar pore ratings (sample nos. 3–4).

EXAMPLE 2

This example illustrates the preparation of filter media of the present invention utilizing a polymer formed from different concentrations of monomers.

Sheets of unsupported microporous PVDF with a pore size of 0.2 micron were prewet with methanol and interleaved with Reemay ® 2250 into rolls. These rolls were introduced into test tubes containing an aqueous solution of 1.5 vol. % PEGDM 600 and either 3, 4, 6, or 9 vol. % DADMAC. A vacuum was applied to remove any residual oxygen from the test tubes, and each of the test tubes was stoppered and irradiated in a $^{60}$Co vault at a dosage of 60,000 rad/hr for 30 hours at 80° F., for a total radiation dose of 1.8 Mrad. The grafted medium from each of the test tubes was rinsed in a deionized water trough for 4 hours to remove unreacted monomer, and dried at 100° C. for 10 minutes.

The hydrophilicity of each of these filter media was evaluated by determining the CWST of each of the filter media. The water flow (l/min/ft$^2$) through each of these filter media at 4 psi was also determined and compared. The obtained CWST and water flow values for each of these various filter media are set forth below.

| Sample No. | Membrane | Monomer Formulation (aq. vol. %) | Pore Rating (microns) | CWST (dynes/cm) | Water Flow (l/min/ft$^2$ at 4 psi) |
|---|---|---|---|---|---|
| 5 | PVDF | 3% DADMAC 1.5% PEGDM 600 | 0.20 | 75–81 | 9.7 |
| 6 | PVDF | 4% DADMAC 1.5% PEGDM 600 | 0.20 | 75–81 | 9.7 |
| 7 | PVDF | 6% DADMAC 1.5% PEGDM 600 | 0.20 | 75–81 | 8.6 |
| 8 | PVDF | 9% DADMAC 1.5% PEGDM 600 | 0.20 | 75–81 | 8.0 |

The filter media of the present invention (sample nos. 5–8) were found to be instantly wettable with water and to demonstrate good water flow properties. As the concentration of the quaternary ammonium group-containing monomer (i.e., DADMAC) increased, the water flow decreased.

EXAMPLE 3

This example illustrates the preparation of filter media in accordance with the present invention utilizing a polymer formed from various combinations of monomers. The CWST, pore size, and water flow properties of the filter media were evaluated and compared.

Sheets of unsupported microporous PVDF with a pore size of 0.2 micron were prewet with methanol and rolled with Reemay ® interleaf 2250 into rolls. These rolls were introduced into test tubes containing an aqueous solution of 6 vol. % DADMAC, 25 vol. % t-butyl alcohol (TBA), 1 vol. % diethylene glycol dimethacrylate (DEGDMA), and either 0, 0.4, or 0.8 vol. % HEMA. A vacuum was applied to remove any residual oxygen from the test tubes, and each of the test tubes was stoppered and irradiated in a $^{60}$Co vault at a dosage of 50,000 rad/hr for either 20 or 40 hours at 80° F., for total radiation doses of either 1.0 Mrad (sample nos. 9, 11, and 13) or 2.0 Mrad (sample nos. 10, 12, and 14). The grafted medium from each of the test tubes was rinsed in a deionized water trough for 4 hours to remove unreacted monomer, and dried at 100° C. for 10 minutes.

The CWST, pore size rating by $K_L$ (H$_2$O), and water flow properties at 2.0 and 4.0 psi for each of the filter media were determined and compared. The obtained values for each of these various filter media are set forth below.

to ensure accuracy. The obtained results are set forth below.

| Sample No. | Membrane | Monomer Formulation (aq. vol. %) | CWST (dynes/cm) | Pore Rating (μm) | Water Flow (1/min/ft²) |
|---|---|---|---|---|---|
| 9 | PVDF | 6% DADMAC<br>25% TBA<br>1% DEGDMA | 75 | 0.2 | 4.7 (2 psi)<br>9.6 (4 psi) |
| 10 | PVDF | 6% DADMAC<br>25% TBA<br>1% DEGDMA | 74 | 0.2 | 5.3 (2 psi)<br>9.7 (4 psi) |
| 11 | PVDF | 6% DADMAC<br>25% TBA<br>1% DEGDMA<br>0.4% HEMA | 81 | 0.2 | 5.4 (2 psi)<br>9.7 (4 psi) |
| 12 | PVDF | 6% DADMAC<br>25% TBA<br>1% DEGDMA<br>0.4% HEMA | 81 | 0.2 | 4.9 (2 psi)<br>10.0 (4 psi) |
| 13 | PVDF | 6% DADMAC<br>25% TBA<br>1% DEGDMA<br>0.8% HEMA | 81 | 0.2 | 4.7 (2 psi)<br>11.1 (4 psi) |
| 14 | PVDF | 6% DADMAC<br>25% TBA<br>1% DEGDMA<br>0.8% HEMA | 81 | 0.2 | 4.9 (2 psi)<br>11.1 (4 psi) |

These results indicate that the present inventive media (sample nos. 9–14) may be prepared using a variety of monomer combinations and that cografting with HEMA helps improve the hydrophilicity of the filter medium. Furthermore, the dose of radiation does not appear to affect the properties of the filter medium.

EXAMPLE 4

This example illustrates the use of the present inventive filter medium to treat BAK-containing solutions and compares the use of such a filter medium with similar filter media which were not prepared in accordance with the present invention.

Solutions containing BAK were filtered through the present inventive PVDF filter medium of Example 1 (sample no. 1), the untreated PVDF filter medium of Example 1 (sample no. 3), and a commercially available treated PVDF filter medium having a negative charge (Millipore Durapore ® filter medium). In particular, BAK of from 50–200 ppm in sterile saline solution was passed through the filter media at a flow rate of 9 ml/min/disc, wherein the filter disc was of 47 mm diameter. The concentration of BAK was measured both upstream and downstream at 210, 242, and 260 nm using a UV spectrometer. The obtained data was then normalized to percent recovery as follows:

% recovery = ([BAK downstream]/[BAK upstream])

The times needed for the BAK downstream concentration to recover to 80% and to 98% of the upstream BAK concentration were also determined for each of the filter media.

The test was conducted by measuring a baseline (upstream) concentration for three minutes of flow time. After the baseline concentration had been established, the upstream concentration was run through the filter medium, and the concentration of BAK in the filtrate (downstream) was measured over the course of 30 minutes. The upstream concentration was then remeasured

| Sample No. | % BAK Recovery 5 Min. | % BAK Recovery 30 Min. | Time Required (sec) 80% BAK Recovery | Time Required (sec) 98% BAK Recovery |
|---|---|---|---|---|
| 1 | 87.6% | 98.6% | 100 | 1180 |
| 3 | 81.5% | 90.0% | 270 | >>1800 |
| Durapore ® | 82.7% | 90.5% | 120 | >>1800 |

These results show that the PVDF filter medium prepared in accordance with the present invention (sample no. 1) performed much better as regards BAK recovery than the PVDF filter media which were not prepared in accordance with the present invention (sample no 3 and Durapore ®).

EXAMPLE 5

This example illustrates the reduced preservative adsorption of PVDF filter media of the present invention as compared to an ungrafted PVDF filter medium.

Solutions containing BAK were filtered through the present inventive filter media of Example 3, as well as the PVDF control of Example 1. The test solutions contained 200 ppm BAK and were passed through the filter media at a flow rate of 9 ml/min/disc, wherein the disc was of 47 mm diameter. The measurements of BAK upstream and downstream of the filter media were carried out as set forth in Example 4.

The amounts of BAK bound to the filter media were determined through use of the method of peak determination, i.e., by weighing the relative masses of paper (bound vs. unbound) cut from the print out of the kinetic trace of concentration (% recovery). Based upon the known flow rate, input concentration, and time to saturation, the total gram amount of BAK challenge to the known mass of each of the filter media could be determined. This allowed for the calculation of the steady-state binding levels in terms of grams bound BAK/grams filter medium (which are expressed in % BAK binding) to compensate for variations in thicknesses of the filter media.

The obtained % BAK binding results for each of the filter media are set forth below.

| Sample No. | BAK Binding |
|---|---|
| 9 | 2.1% |
| 10 | 2.1% |
| 11 | 3.2% |
| 12 | 1.3% |
| 13 | 2.7% |
| 14 | 2.6% |
| 3 | 8.4% |

These results demonstrate that BAK binding is greatly reduced in the present inventive filter media (sample nos. 9-14) as compared to the similar filter medium which was not prepared in accordance with the present invention (sample no. 3).

EXAMPLE 6

This example further illustrates the reduced preservative adsorption of PVDF filter media of the present invention as compared to an ungrafted PVDF filter medium.

Solutions containing preservative methyl paraben (MPB) were filtered through the present inventive filter medium of Example 1, as well as other similar PVDF filter media which possessed either no charge (untreated PVDF filter media) or a negative charge (Pall Fluorodyne ® filter media). The pore ratings of all of the filter media were the same. The test solutions contained 6 ppm MPB and were passed through the filter media at a flow rate of 5 ml/min/disc, wherein the disc was of 47 mm diameter. The measurements of MPB upstream and downstream of the filter media were carried out in a manner similar to that for BAK as set forth in Example 4.

The amounts of MPB bound to the filter media were determined through use of the method of peak determination, i.e., by weighing the relative masses of paper (bound vs. unbound) cut from the print out of the kinetic trace of concentration (% recovery). Based upon the known flow rate, input concentration, and time to saturation, the total gram amount of MPB challenge to the known mass of each of the filter media could be determined. This allowed for the calculation of the steady-state binding levels in terms of grams bound MPB/grams filter medium (which are expressed in % MPB binding) to compensate for variations in thicknesses of the filter media.

The obtained % MPB binding results for each of the filter media are set forth below.

| Sample No. | Membrane | Monomer Formulation (aq. vol. %) | MPB Binding |
|---|---|---|---|
| 1 | PVDF | 6.0% DADMAC 1.5% PEGDM 600 | 0.0003% |
| 15 | PVDF | — | 0.0077% |
| 16 | PVDF | — | 0.0049% |
| 17 | PVDF | — | 0.0025% |
| 18 | PVDF | Fluorodyne ® | 0.0008% |

These results demonstrate that MPB binding is greatly reduced in the present inventive filter medium (sample no. 1) as compared to the similar filter media which were not prepared in accordance with the present invention (sample nos. 15-18).

EXAMPLE 7

This example illustrates the reduced preservative adsorption characteristics of the present inventive PVDF filter medium as compared to untreated PVDF and nylon filter media.

The BAK adsorption characteristics of the present inventive filter medium of Example 1 was compared to that of untreated PVDF and nylon filter media in the manner set forth in Example 4. The obtained % BAK binding results are set forth below.

| Sample No. | Membrane | Monomer Formulation (aq. vol. %) | BAK Binding |
|---|---|---|---|
| 1 | 0.2 micron pore size PVDF | 6.0% DADMAC 1.5% PEGDM 600 | 1.4% |
| 19 | 0.2 micron pore size PVDF | — | 8.5% |
| 20 | 0.2 micron pore size nylon on polyester substrate | — | 3.9% |
| 21 | 0.45 micron pore size nylon on polyester substrate | — | 3.3% |

These results demonstrate the BAK retention superiority of the present inventive filter medium (sample no. 1) as compared to other filter media (sample nos. 19-21).

All of the references cited herein are hereby incorporated in their entireties by reference.

While this invention has been described with an emphasis upon preferred embodiments, it will be obvious to those of ordinary skill in the art that variations in the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A filter medium comprising a microporous polyvinylidene fluoride membrane and a polymer containing positively charged quaternary ammonium groups substantially only covalently bonded to said membrane in a concentration sufficient to provide a surface of said membrane with a positive charge such that there is minimal susceptibility to the extraction of said polymer.

2. The filter medium of claim 1, wherein said polymer is prepared from diallyldimethylammonium chloride.

3. The filter medium of claim 2, wherein said polymer is prepared from diallyldimethylammonium chloride and an acrylate or methacrylate.

4. The filter medium of claim 3, wherein said polymer is prepared from diallyldimethylammonium chloride, an acrylate, and a methacrylate.

5. The filter medium of claim 3, wherein said acrylate is selected from the group consisting of hydroxypropyl acrylate, hydroxyethyl acrylate, and diethylene glycol diacrylate, and said methacrylate is selected from the group consisting of hydroxyethyl methacrylate, polyethylene glycol dimethacrylate 600, hydroxypropyl methacrylate, and diethylene glycol dimethacrylate.

6. The filter medium of claim 3, wherein said polymer is prepared from diallyldimethylammonium chloride and hydroxyethyl methacrylate.

7. The filter medium of claim 6, wherein the volume ratio of said diallyldimethylammonium chloride and said hydroxyethyl methacrylate is from about 3:1 to about 15:1.

8. The filter medium of claim 3, wherein said polymer is prepared from diallyldimethylammonium chloride and polyethylene glycol dimethacrylate 600.

9. The filter medium of claim 8, wherein the volume ratio of said diallyldimethylammonium chloride and said polyethylene glycol dimethacrylate 600 is from about 3:1 to about 15:1.

10. The filter medium of claim 1, wherein said membrane is exposed to gamma radiation and then contacted with a solution of monomers in a solvent to prepare said polymer containing positively charged quaternary ammonium groups covalently bonded to said membrane.

11. The filter medium of claim 10, wherein said solution contains a quaternary ammonium group-containing monomer and a polar, nonionic monomer in a volume ratio of from about 3:1 to about 15:1.

12. The filter medium of claim 10, wherein said solution contains diallyldimethylammonium chloride and hydroxyethyl methacrylate in a volume ratio of from about 3:1 to about 15:1.

13. The filter medium of claim 10, wherein said solution contains diallyldimethylammonium chloride and polyethylene glycol dimethacrylate 600 in a volume ratio of from about 3:1 to about 15:1.

14. A method of treating a composition, which method comprises filtering a composition through a filter medium comprising a microporous polyvinylidene fluoride membrane and a polymer containing positively charged quaternary ammonium groups substantially only covalently bonded to said membrane in a concentration sufficient to provide a surface of said membrane with a positive charge such that there is minimal susceptibility to the extraction of said polymer.

15. The method of claim 14, wherein said composition is an ophthalmic solution.

16. The method of claim 15, wherein said ophthalmic solution contains active ingredients and said method does not substantially remove said active ingredients.

17. The method of claim 16, wherein said ophthalmic solution contains benzalkonium chloride which is substantially retained in the filtrate after said ophthalmic solution is filtered through said filter medium.

18. The method of claim 14, wherein said composition is a pharmaceutical composition.

19. A filter cartridge comprising a filter medium comprising a microporous polyvinylidene fluoride membrane and a polymer containing positively charged quaternary ammonium groups substantially only covalently bonded to said membrane in a concentration sufficient to provide a surface of said membrane with a positive charge such that there is minimal susceptibility to the extraction of said polymer.

20. The filter cartridge of claim 19, wherein said filter medium is interleaved with support layers.

21. The filter cartridge of claim 19, wherein said filter medium is unsupported.

22. A method of treating a composition, which method comprises filtering a composition through a filter medium comprising a microporous polyvinylidene fluoride membrane and a polymer containing positively charged quaternary ammonium groups substantially only covalently bonded to said membrane in a concentration sufficient to provide a surface of said membrane with a positive charge such that there is minimal susceptibility to the extraction of said polymer, wherein said polymer is prepared from (a) diallyldimethylammonium chloride, (b) an acrylate selected from the group consisting of hydroxypropyl acrylate, hydroxyethyl acrylate, and diethylene glycol diacrylate, and (c) a methacrylate selected from the group consisting of hydroxyethyl methacrylate, polyethylene glycol dimethacrylate 600, hydroxypropyl methacrylate, and diethylene glycol dimethacrylate.

23. The method of claim 22, wherein said composition is an ophthalmic solution.

24. The method of claim 23, wherein said ophthalmic solution contains active ingredients and said method does not substantially remove said active ingredients.

25. The method of claim 24, wherein said ophthalmic solution contains benzalkonium chloride which is substantially retained in the filtrate after said ophthalmic solution is filtered through said filter medium.

26. The method of claim 22, wherein said composition is a pharmaceutical composition.

27. A filter cartridge comprising a filter medium comprising a microporous polyvinylidene fluoride membrane and a polymer containing positively charged quaternary ammonium groups substantially only covalently bonded to said membrane in a concentration sufficient to provide a surface of said membrane with a positive charge such that there is minimal susceptibility to the extraction of said polymer, wherein said polymer is prepared from (a) diallyldimethylammonium chloride, (b) an acrylate selected from the group consisting of hydroxypropyl acrylate, hydroxyethyl acrylate, and diethylene glycol diacrylate, and (c) a methacrylate selected from the group consisting of hydroxyethyl methacrylate, polyethylene glycol dimethacrylate 600, hydroxypropyl methacrylate, and diethylene glycol dimethacrylate.

28. The filter cartridge of claim 27, wherein said filter medium is interleaved with support layers.

29. The filter cartridge of claim 27, wherein said filter medium is unsupported.

* * * * *